US012779128B2

(12) United States Patent
Eardley

(10) Patent No.: US 12,779,128 B2
(45) Date of Patent: Nov. 3, 2026

(54) ARRANGEMENT FOR A DRUG DELIVERY DEVICE AND DRUG DELIVERY DEVICE

(71) Applicant: Sanofi, Paris (FR)

(72) Inventor: Zoë Georgina Eardley, Warwick (GB)

(73) Assignee: SANOFI, Paris (FR)

( * ) Notice: Subject to any disclaimer, the term of this patent is extended or adjusted under 35 U.S.C. 154(b) by 1071 days.

(21) Appl. No.: 17/782,826

(22) PCT Filed: Dec. 11, 2020

(86) PCT No.: PCT/EP2020/085731

§ 371 (c)(1),
(2) Date: Jun. 6, 2022

(87) PCT Pub. No.: WO2021/116390

PCT Pub. Date: Jun. 17, 2021

(65) Prior Publication Data

US 2023/0027933 A1 Jan. 26, 2023

(30) Foreign Application Priority Data

Dec. 13, 2019 (EP) .................................... 19306643

(51) Int. Cl.
*A61M 5/315* (2006.01)

(52) U.S. Cl.
CPC ................................ *A61M 5/3155* (2013.01)

(58) Field of Classification Search
CPC .................................................. A61M 5/3155
See application file for complete search history.

(56) References Cited

U.S. PATENT DOCUMENTS

2012/0289909 A1 11/2012 Raab et al.
2014/0018745 A1 1/2014 Plumptre
(Continued)

FOREIGN PATENT DOCUMENTS

CN 102834133 A 12/2012
CN 106999658 A 8/2017
(Continued)

OTHER PUBLICATIONS

Notice of Reasons for Rejection, JP Patent Application No. 2022-535484, dated Nov. 12, 2024, pp. 1-14 (with pp. 1-7 being a translation).

(Continued)

*Primary Examiner* — Dung T Ulsh
(74) *Attorney, Agent, or Firm* — Bond, Schoeneck & King, PLLC

(57) ABSTRACT

An arrangement for a drug delivery device is provided, the arrangement comprising: a housing having a proximal end and a distal end, a dose setting member which is rotatable relative to the housing for a dose setting operation in order to set a dose of drug to be delivered, a tracking member, and a guide track. Wherein the tracking member is operatively coupled or coupleable to the dose setting member, or wherein b) the dose setting member is a tracking member. The guide track is configured to form a guiding interface to guide and/or drive movement of the tracking member. The tracking member can be displaced towards an axial tracking member end position during the dose setting operation, wherein the distance by which the tracking member is displaced towards the axial tracking member end position depends on the size of the set dose.

17 Claims, 7 Drawing Sheets

(56) References Cited

U.S. PATENT DOCUMENTS

| | | | | |
|---|---|---|---|---|
| 2016/0067412 | A1 | 3/2016 | Bayer et al. | |
| 2017/0136188 | A1 | 5/2017 | Marsh | |
| 2017/0259006 | A1* | 9/2017 | Avery | A61M 5/20 |
| 2017/0312443 | A1 | 11/2017 | Avery et al. | |
| 2018/0050159 | A1 | 2/2018 | Enge et al. | |
| 2018/0071460 | A1 | 3/2018 | Rekaya et al. | |
| 2018/0193568 | A1 | 7/2018 | Hayton et al. | |

FOREIGN PATENT DOCUMENTS

| | | | |
|---|---|---|---|
| CN | 107427643 | A | 12/2017 |
| CN | 110099711 | A | 8/2019 |
| JP | 2016514591 | A | 5/2016 |
| JP | 2016514603 | A | 5/2016 |
| WO | WO 2016/083380 | A1 | 6/2016 |
| WO | WO 2016/139023 | A1 | 9/2016 |
| WO | WO 2018/115313 | A1 | 6/2018 |

OTHER PUBLICATIONS

Second Office Action, CN Patent Application No. 202080086599.9, dated Sep. 13, 2024, pp. 1-15 (with pp. 1-9 being a translation).

International Preliminary Report on Patentability in International Appln. No. PCT/EP2020/085731, mailed on Jun. 23, 2022, 8 pages.

International Search Report and Written Opinion in International Appln. No. PCT/EP2020/085731, mailed on Jan. 13, 2021, 10 pages.

* cited by examiner

ARRANGEMENT FOR A DRUG DELIVERY DEVICE AND DRUG DELIVERY DEVICE

CROSS REFERENCE TO RELATED APPLICATIONS

The present application is the national stage entry of International Patent Application No. PCT/EP2020/085731, filed on Dec. 11, 2020, and claims priority to Application No. EP 19306643.8, filed on Dec. 13, 2019, the disclosures of which are incorporated herein by reference.

TECHNICAL FILED

The present disclosure relates to an arrangement for a drug delivery device and a drug delivery device, especially a device comprising the arrangement.

BACKGROUND

Drug delivery devices often include end-of-content tracker mechanisms which prevent that the devices can be used for delivery operations, which attempt to deliver a drug quantity which exceeds the one available in a reservoir. Usually, these mechanisms are designed to prevent the setting of a dose which exceeds the quantity of drug remaining in a reservoir.

SUMMARY

The present disclosure provides a novel arrangement for a drug delivery device which facilitates provision of an improved drug delivery device. Moreover, a drug delivery device comprising the arrangement is provided.

It should be noted that the present disclosure is not restricted to the claims and may contain other embodiments which are broader than the ones defined in the claims. Of course, features which are disclosed in conjunction with different embodiments can also be combined with one another and/or with the features of yet further embodiments. The scope of protection for the present disclosure, however, is defined by the appended claims.

In an embodiment, the arrangement for the drug delivery device comprises a housing having a proximal end and a distal end. The arrangement further comprises a dose setting member. The dose setting member is preferably rotatable relative to the housing for a dose setting operation in order to set a dose of drug to be delivered, e.g. by the drug delivery device, and/or in a subsequent dose dispensing or dose delivery operation for delivering the set dose. For setting the dose, the dose setting member may be rotatable in one rotational direction, e.g. an incrementing direction to increase the size of the set dose, away from an initial position towards a dose set position. When in the initial position a rotation counter to the incrementing direction may be prevented. When a dose of a particular size has been set, i.e. in the dose set position, rotation counter to the incrementing direction may be allowed in order to reduce the set dose, e.g. in case it does not match the intended size. Also, further increasing of the set dose from the dose set position may be allowed by continuing rotation in the incrementing direction, e.g. up to a maximum settable dose. The dose setting member may exhibit a user interface of the arrangement. Consequently, it may be arranged to be touched directly by a user for operating the arrangement.

The arrangement further comprises a tracking member. The tracking member may be a member of an end-of-content tracker mechanism mentioned further above. A position of the tracking member relative to the housing, particularly an axial position, may be indicative for the remaining total dose which can be still be set and delivered using the arrangement.

The tracking member may be a member different from the dose setting member. In other words, the tracking member may be operatively coupled or coupleable to the dose setting member, e.g. directly or indirectly. Particularly, rotation of the dose setting member may be converted into movement of the tracking member with respect to the housing, particularly axial movement. The tracking member may rotate relative to the housing or be rotationally locked relative to the housing during the axial movement. Alternatively, the dose setting member itself may be the tracking member. Thus, one member may serve as a setting member and as a tracking member.

The dose setting member may be unitary or it may have a plurality of parts which are connected to one another, expediently rigidly. In case the dose setting member has a plurality of parts these parts, during operation of the arrangement, expediently act as a single member, especially during the dose setting operation, a dose correcting operation, a reset operation and/or a dose delivery operation.

The arrangement further comprises a guide track. The guide track is expediently configured to form or define a guiding interface to guide and/or drive movement of the tracking member, e.g. to guide and/or drive movement relative to the housing and/or another member of the arrangement, where the member may comprise the guide track. The guiding interface may be established between the guide track and an interface feature which mechanically cooperates with the guide track. One of the interface feature and the guide track may be provided on the tracking member. The other one of the interface feature and the guide track may be provided on another member of the arrangement or the housing. The guide track may be a helical track or thread.

The arrangement is configured such that the tracking member is displaced towards a, preferably axial, tracking member end position, e.g. a position of the tracking member relative to the housing or another member of the arrangement, during the dose setting operation. The distance by which the tracking member is displaced towards the axial tracking member end position may depend on, e.g. be proportional to, the size of the dose which is set during the dose setting operation.

When the tracking member has reached the tracking member end position, further rotation of the dose setting member in the direction which would increase the size of the set dose may be prevented, e.g. by the tracking member abutting an axial and/or rotational end stop. A decrease in the set dose is, preferably, still allowed when the tracking member is in its end position.

By using the dose setting member as a tracking member or a tracking member operatively coupled to the dose setting member, the tracking member may be arranged relatively close to an outer surface of the arrangement. Thus, once the tracking member is in its end position a load exerted by the user onto the tracking member in an attempt to increase the set dose, which is, of course, blocked, by the tracking member, may be transferred to components which have a larger diameter than components which are arranged further in the interior of the arrangement. For example, the load may be reacted by the housing. On account of the larger diameter, the force acting on or exerted by the tracking member which needs to be reacted to prevent further rotation of the tracking member may be smaller as compared to cases where the tracking member acts in a region of smaller diameter in the interior of the arrangement.

The dose setting member is expediently provided to be manipulated by the user for setting the dose. Consequently, it preferably provides a portion of an exterior surface of the arrangement or the drug delivery device. If the tracking member is close to an outer surface, so may be the guiding interface. Accordingly, as compared to components of the arrangement which are arranged further in the interior. The tracking member may be guided by the interface at a comparatively large diameter. This may be advantageous, since the tracking member may be arranged pretty close to that part of the arrangement where the user exerts force in order to set the dose, i.e. the outer surface of the dose setting member which is accessible from the exterior of the device or the arrangement.

In an embodiment, during the dose setting operation, the dose may be varied in an incremented manner, e.g. increased or decreased, in whole-number multiples of a unit increment. The number of different doses which can be set in a dose setting operation and delivered in a dose delivery operation may be greater than or equal to one of the following values: 5, 10, 15. Alternatively or additionally, the number of different doses which can be set in a dose setting operation and delivered in a dose delivery operation may be less than or equal to one of the following values: 20, 19, 18, 17, 16.

In an embodiment, the axial tracking member end position is defined by the guide track. For example, an angular facing end surface of the guide track may define an end stop surface, the end stop surface being abutted by a corresponding surface of the interface feature when the tracking member has reached the end position and, consequently, further rotation in that direction which increases the set dose is no longer possible.

In an embodiment, the arrangement is configured such that the relative position of the tracking member with respect to the axial tracking member end position is constant during the dose delivery operation.

In an embodiment, the axial tracking member end position is defined by an end stop which is rotationally and/or axially secured to the housing e.g. during the dose setting operation and/or the dose delivery operation. The end stop may be separated from the guide track and/or the interface feature.

In an embodiment, the arrangement comprises a further member. The further member, as the dose setting member, may be a part of the dose setting and drive mechanism of the arrangement. The further member may be a member which is operatively coupled to an energy storage member which is designed to store energy during the dose setting operation on account of the force provided by the user. The energy storage member may be a spring such as a drive spring, e.g. a torsion spring. The spring may be designed to provide the force required for a dose delivery operation, which is performed after the dose has been set, in order to deliver the set dose. The further member may be a dose indication member such as a number sleeve, for example.

In an embodiment, the dose setting member may be operatively coupled or coupleable, particularly during the dose setting operation, to the further member in order to transfer force from the dose setting member to the further member. The coupling may be effected via a clutch mechanism. The clutch mechanism may be configured to couple, preferably to releasably couple, the further member to the dose setting member, e.g. during the dose setting operation.

The clutch mechanism may be a setting clutch mechanism. The clutch mechanism may comprise a clutch force transfer interface via which force is transferred from the dose setting member to the further member, particularly during the dose setting operation. For this purpose, clutch features locked, e.g. rotationally locked, relative to the dose setting member and to the further member may abut. The clutch feature for the dose setting member may be provided on a member rotationally locked to the dose setting member, e.g. the activation member, which will be discussed below. The clutch feature for the further member may be provided on the further member. Thus, when the further member and the dose setting member are coupled, a first clutch feature of the activation member and a second clutch feature of the further member may abut. The coupling may be released by relative axial movement between the first and second clutch features. During the dose setting operation, the dose setting member may be rotationally locked to the further member, especially by the clutch mechanism. The rotational lock may be operational in both rotational directions such that the further member follows rotational movement of the dose setting member in both rotational directions, e.g. for increasing and decreasing the size of the set dose.

For the dose delivery operation, the coupling between the further member and the dose setting member may be released. When the coupling is released, there may be no force transfer from the dose setting member to the further member and/or vice versa. When the coupling is released, the further member may be allowed to rotate relative to the dose setting member.

In an embodiment, force is transferred from the dose setting member to the tracking member via a tracking member force transfer interface. This interface may be the guiding interface or a different interface, such as a splined interface. The dose setting member may be directly coupled to the tracking member via this interface. Alternatively, the dose setting member may be indirectly coupled to the tracking member via this interface e.g. via an activation member which will be discussed further below.

In an embodiment, the tracking member force transfer interface is arranged closer to an outer surface of the dose setting member, particularly a surface which is configured to be touched by a user, than the clutch force transfer interface, particularly as seen along the force transfer path from the outer surface to the respective force transfer interface. In other words, the force transfer path from the outer surface of the dose setting member to the clutch force transfer interface may be longer than the force transfer path from the outer surface of the dose setting member to the tracking member force transfer interface.

In an embodiment, the tracking member force transfer interface is arranged proximally relative to the clutch force transfer interface. In other words, the tracking member force transfer interface may be arranged closer to the proximal end of the arrangement or the device than the clutch force transfer interface.

Accordingly, the force transfer to the tracking member may be effected close to the proximal end. Moreover, a force acting on the tracking member in the end position may be reacted by the housing or be transferred to the housing sooner than if the tracking member were arranged further away from the dose setting member as seen along the force transfer path or further away from the proximal end. Moreover, the force does not act on the clutch mechanism which is advantageous since a user attempting to increase the dose beyond the limit defined by the tracking member end position may exert considerable force which may destroy or damage components of the arrangement.

In an embodiment, the guide track is radially outwardly offset relative to the first clutch feature and/or the second clutch feature, e.g. at least in the dose setting operation.

In an embodiment, the guide track is proximally offset relative to the first clutch feature and/or the second clutch feature, e.g. at least in the dose setting operation.

In an embodiment, the arrangement further comprises a piston rod. The piston rod may be a lead screw. The piston rod may be configured to be displaced in the distal direction with respect to the housing towards a distal end position for delivering the previously set dose in the dose delivery operation. The distal end position may be the position, in which further dose delivery operations and/or further dose setting operations are no longer possible. Thus, when the piston rod is in the distal end position, it cannot be displaced anymore in the distal direction or away from the proximal end.

In an embodiment, the arrangement comprises a drive member. The drive member may be engaged to the piston rod in order transfer force to the piston rod for the delivery operation. The drive member may be rotationally locked to the piston rod. The force transferred to the piston rod may be or may comprise force transferred to the piston rod from the user and/or force transferred to the piston rod from an energy storage member, such as a spring. If an energy storage member is used, the energy stored in the member may be increased during the dose setting operation. Therefore, the user may provide force for the delivery operation during the dose setting operation.

In an embodiment, the length of the guide track is characteristic for the distance the piston rod can be displaced axially relative to the housing from a proximal initial position to the distal end position. Thus, the length of the guide track may be characteristic for the entire displacement distance which is available for displacing the piston rod in order to perform delivery operations. In the initial position, a reservoir of the drug delivery device may be still full with no drug having been dispensed yet from the reservoir. When the piston rod is in the distal end position, the drug delivery device or the reservoir is considered empty.

In an embodiment, a distance of the tracking member from the tracking member axial end position before the dose setting operation is commenced may be determined by, e.g. be proportional to, the distance between the current position of the piston rod and the distal end position of the piston rod.

In an embodiment, the relative position between the tracking member and the axial tracking member end position is constant during the dose delivery operation. Alternatively or additionally, in the dose delivery operation there may be no relative movement between the guide track or the interface feature and the tracking member.

In an embodiment, the tracking member is arranged relative to the housing such that it overlaps with the dose setting member axially. Accordingly, as seen along the longitudinal axis which may extend from the proximal end to the distal end of the housing, there is an axial position, where, when viewed in the radial direction from that axial position, a section of the tracking member and a section of the dose setting member is arranged. A section of the housing may be arranged between the dose setting member and the tracking member.

The arrangements which are specified above or further below of the tracking member relative to the housing or other components or members may be present in the initial position of the tracking member and in the axial tracking member end position or in just one of these positions such as in the initial position or in the axial tracking member end position. The arrangements which are specified above or further below of the tracking member relative to the housing or relative other components or members may be present at least in the dose setting operation, such as only in the dose setting operation or in the dose setting operation and the dose delivery operation.

In an embodiment, the tracking member is arranged between a surface of the housing and a surface of the dose setting member. The tracking member may be arranged between an outer surface of the housing and an inner surface of the dose setting member.

In an embodiment, the housing defines a portion of an exterior surface of the arrangement. At the proximal end of the housing a cartridge unit may be secured to the housing. The housing may have a tubular shape and/or may house further components of the dose setting and drive mechanism such as the drive spring, the drive member and/or the piston rod.

In an embodiment, the dose setting member is axially locked to the housing but rotatable relative to the housing for the dose setting operation. In this case, the axial position of the dose setting member relative to the housing does not change when the dose setting operation is being performed. The dose setting member may be permanently axially secured to the housing.

In an embodiment, particularly if the dose setting member is the tracking member, the dose setting member may be axially displaced relative to the housing during the dose setting operation by a distance which is characteristic for the size of the currently set dose.

In an embodiment, the tracking member is arranged in the proximal end region of the housing.

This facilitates having a short force transfer path between the dose setting member and the tracking member. Specifically, the tracking member may be arranged closer to the proximal end of the housing than to the distal end of the housing.

In an embodiment, the dose setting member is engaged to the housing by the guide track. In particular, this is useful if the dose setting member is the tracking member.

In an embodiment, the dose setting member is configured to be touched by the user, e.g. for the dose setting operation, such as for performing the dose setting operation. Particularly, a radially facing surface of the dose setting member may be touched by the user for rotating the dose setting member relative to the housing in the dose setting operation. In other words, the dose setting member may provide a portion of an exterior surface of the arrangement.

In an embodiment, the arrangement comprises activation member. The activation member may be configured to be operated in order to perform a dose delivery operation, e.g. for delivering the previously set dose, such as the dose set in the dose setting operation. The activation member may be rotationally locked to the dose setting member. Accordingly, activation member and dose setting member may co-rotate regardless of the rotation direction of rotation relative to the housing. The activation member may be axially movable relative to the dose setting member, e.g. in the distal direction and/or to initiate the dose delivery operation. The activation member may provide a portion of an exterior surface of the arrangement.

In an embodiment, during the dose setting operation, the axial position of the activation member relative to the housing is constant. A proximal surface of the activation member may form the proximal end of the arrangement or the entire device. Accordingly, the length of the arrangement does not change significantly during the dose setting operation or not at all.

In an embodiment, the activation member protrudes proximally from the dose setting member. The activation member may protrude from the dose setting member regardless of the position of the tracking member relative to the housing. During dose setting, e.g. if the dose setting member is the tracking member, the distance between the proximal end of the dose setting member and the proximal end of the activation member may be reduced, particularly in an amount characteristic for the currently set dose. Accordingly, the length by which the activation member protrudes proximally from the dose setting member should be greater than the axial distance between the axial tracking member end position and the initial position of the dose setting member.

In an embodiment, the activation member is configured to be touched and/or moved by the user for the dose delivery operation, e.g. for initiating and/or for performing the dose delivery operation. The activation member may be moved from a first position to a second position, e.g. relative to the housing and/or axially such as only axially. The first position may be proximally offset relative to the second position. The arrangement may be configured such that during the movement of the activation member from the first position to the second position, the clutch mechanism is released. In other words, during the movement of the activation member from the first position to the second position, the further member and the dose setting member may be decoupled from one another, e.g. rotationally. Thus, in the second position, the further member may be allowed to rotate relative to the dose setting member. Alternatively or additionally, the dose setting member may be rotationally locked relative to the housing. Consequently, in the second position of the activation member, the dose setting member and the further member may be uncoupled and/or the dose setting member may be rotationally locked relative to the housing. The activation member may be biased towards the first position, when it is in the second position, e.g. by a resilient member. Thus, the first position may be the regular position of the activation member.

Preferably, the rotational lock between the dose setting member and the housing is established before the clutch mechanism is released. This prevents that, when the clutch mechanism has been released, the user could change the rotational position of the dose setting member which may have direct or indirect influence on the position of the tracking member relative to the tracking member end position. The dose setting member may be rotationally locked relative to the housing by a rotational lock established between locking features of the dose setting member and locking features provided on the housing.

In an embodiment, the tracking member is arranged between the area where the dose setting member is axially locked relative to the housing and the proximal end of the housing.

In an embodiment, the tracking member is axially locked with respect to the housing when the activation member is moved from the first position into the second position. Alternatively, the tracking member may follow axial movement of the activation member relative to the housing from the first position into the second position.

In an embodiment, the tracking member is engaged to at least one member which defines at least a portion of an outer or exterior surface of the arrangement. Preferably, the at least one member is a member other than the housing, e.g. the dose setting member and/or the activation member. The tracking member may be engaged to a plurality of members which define at least a portion of an outer or exterior surface of the arrangement, e.g. to two members. The two members may include the housing.

In an embodiment, the tracking member is engaged to the dose setting member. The tracking member may be engaged to the housing, additionally.

In an embodiment, the tracking member is engaged to the activation member. The tracking member may be engaged to the housing, additionally.

In an embodiment, the guide track is provided on the housing, on the dose setting member, on the activation member or on the tracking member. The interaction feature for establishing the guiding interface may be arranged on the tracking member or on the member which the tracking member engages. Expediently, guide track and interaction feature are arranged on different components or members.

In an embodiment, the guiding interface is established between the tracking member and the housing, between the tracking member and the activation member, or between the tracking member and the dose setting member.

In an embodiment, the tracking member is the last dose member and/or a nut member, such as a last dose nut.

In an embodiment, the arrangement comprises an energy storage member, e.g. a spring. The energy storage member may be configured to store energy for conducting a dose delivery operation. During the dose setting operation, the energy stored in the energy storage member may be increased, e.g. by energy provided by the user.

In an embodiment, a drug delivery device is provided, where the device preferably comprises the arrangement as discussed above. The drug delivery device further comprises a reservoir containing a drug and/or a reservoir retainer being provided to retain a reservoir containing a drug. The reservoir may be a cartridge. The reservoir expediently contains drug in an amount sufficient for delivering a plurality of doses, preferably even if the maximum dose is set each time. The device may be an injection device, e.g. a pen-type injector. The device may be a reusable device or a disposable device. The device may be needle based. The dose delivery operation may be partly or entirely driven by energy provided by the energy storage member.

Features which are disclosed in conjunction with different embodiments can be combined with one another. For example, features disclosed for the drug delivery device do also apply for the arrangement and vice versa.

“Distal” is used herein to specify directions, ends or surfaces which are arranged or are to be arranged to face towards the dispensing end of the arrangement, the drug delivery device or components thereof and/or are directed or are to be directed away from or face away from the proximal end. On the other hand, “proximal” is used to specify directions, ends or surfaces which are arranged or are to be arranged to face away from the dispensing end or the distal end of the arrangement, the drug delivery device or components thereof. The distal end may be the end closest to the dispensing end and/or furthest away from the proximal end. The proximal end may be the end furthest away from the dispensing end. A proximal surface may face away from the distal end and/or towards the proximal end. A distal surface may face towards the distal end and/or away from the proximal end.

In a particularly advantageous embodiment, an arrangement for a drug delivery device is provided, the arrangement comprising:

a housing having a proximal end and a distal end, a dose setting member which is rotatable relative to the housing for a dose setting operation in order to set a dose of drug to be delivered, wherein a) the arrangement further comprises a tracking member, wherein the tracking member is operatively coupled or coupleable to the dose setting member, or wherein b) the dose setting member is a tracking member, wherein the arrangement further comprises a guide track, wherein the guide track is configured to form a guiding interface to guide and/or drive movement of the tracking member, wherein the arrangement is configured such that the tracking member is displaced towards an axial tracking member end position during the dose setting operation, wherein the distance by which the tracking member is displaced towards the axial tracking member end position depends on the size of the set dose.

Further features, advantages and expediencies will become apparent from the following description of the exemplary embodiments in conjunction with the drawings.

Figure 1:
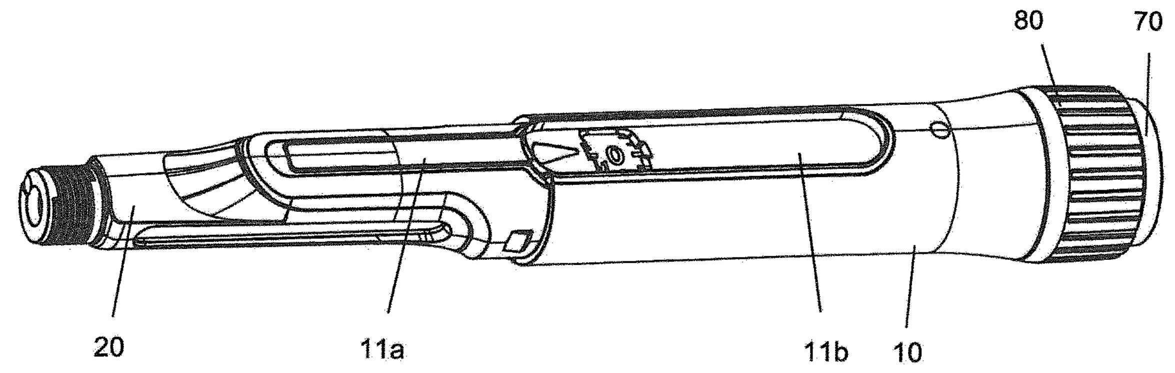
FIG. 1 shows a perspective view of an embodiment of a drug delivery device.

Identical elements, identically element acting elements and elements of the same kind may be provided with the same reference numerals in the drawings. Moreover, it should be appreciated that the drawings just illustrate some embodiments of the present disclosure. The disclosed concepts may be applicable to drug delivery devices of designs different from the ones disclosed below as well.

DETAILED DESCRIPTION

Figure 2:
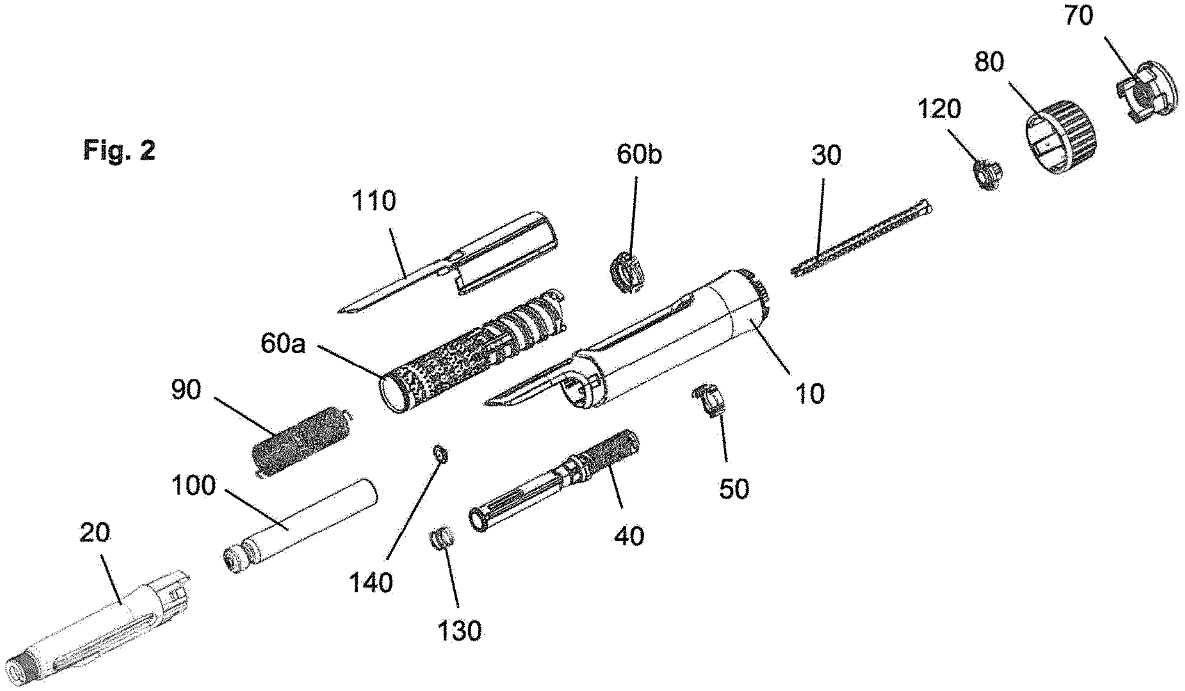
FIG. 2 shows an exploded view of the components of the device of FIG. 1.

FIG. 1 shows a drug delivery device in the form of an injection pen. The device has a distal end (left end in FIG. 1) and a proximal end (right end in FIG. 1). The component parts of the drug delivery device are shown in FIG. 2. The drug delivery device comprises a body or housing 10, a cartridge holder 20, a lead screw (piston rod) 30, a drive sleeve or driver 40, a tracking member (nut) 50, a dose indicator (number sleeve) 60, an activation member (button) 70, a dose setting member (dial grip or dose selector) 80, a torsion spring 90, a cartridge 100, a gauge element 110, a clutch plate 120, a clutch spring 130 and a bearing 140. A needle arrangement (not shown) with a needle hub and a needle cover may be provided as additional components, which can be exchanged. All components are located concentrically about a common principal axis I (FIG. 3*b*) of the mechanism or the device.

The housing 10 or body is a generally tubular casing element having a proximal end, e.g. with an enlarged diameter. The housing 10 provides location for the liquid medication or drug cartridge 100 and cartridge holder 20. As shown in FIGS. 1 and 2, the housing comprises a first window 11*a* and a second window (or lens) 11 *b* which are incorporated into the housing body e.g. by twin-shot moulding. The windows 11*a*, 11*b* may be moulded during a first shot in a translucent (and preferably transparent) material, and the outer cover of the housing is moulded during a second shot in an opaque material.

In the embodiment of FIGS. 1 to 3*b* the housing comprises an insert 12 as an integral part located as an inner wall near the distal end of the housing. The insert 12 may be moulded in the translucent material. As an alternative, the insert or parts thereof may be formed in the opaque material or as a separate component part as depicted in the embodiment of FIG. 4.

The insert 12 is a cup-shaped component part with a sidewall 13 and a tube 14 extending through the insert 12, thus forming an annular space there between. Arms 15 extend radially outwards from the sidewall 13. A bottom wall 16 connects the sidewall 13 and the tube 14 on the distal side of the insert 12, whereas the opposite proximal side is open. The insert 12 has various interfaces. For example, the tube 14 of insert 12 comprises an inner thread 17 engaging the piston rod 30. In addition the radial space between the tube 14 and the outer sidewall 13 may provide a bearing area receiving the drive spring 90 and the clutch spring 130. Further, spline teeth 18 are provided on the insert 12 engaging corresponding spline teeth 41 at the distal end of drive sleeve 40. Teeth 18 interact with drive sleeve 40 to rotationally couple and de-couple the drive sleeve and the housing 10.

Figure 4:
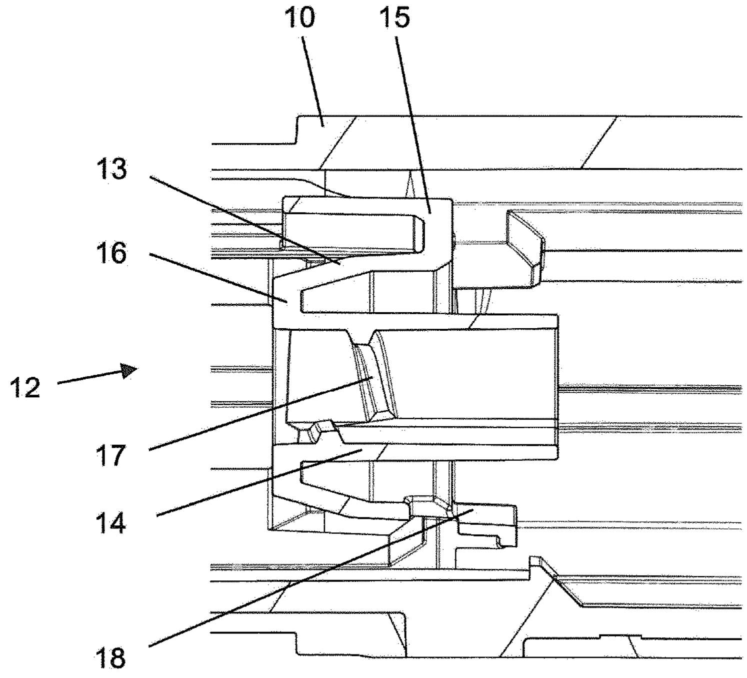
FIG. 4 shows, in a sectional view, a detail of a device according to another embodiment.

In the embodiment of FIG. 4, the insert is an integral part of an inner housing shell which inner shell is partially surrounded by an external housing shell. The shells may be formed by two consecutive shots of injection moulding such that the shells are permanently attached to each other. For example, the inner shell is formed from a transparent or translucent material, whereas the outer shell is formed from an opaque material.

Figure 5A:
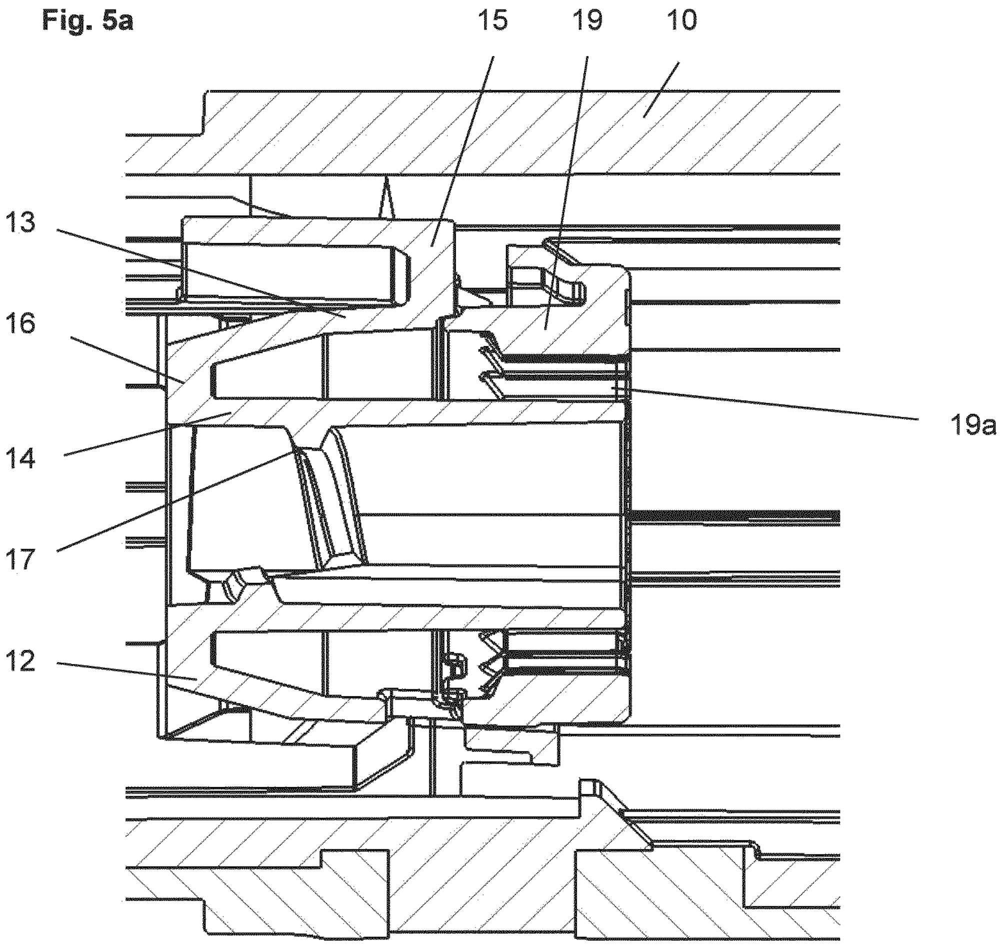
FIG. 5*a* shows in a sectional view a detail of a device according to yet another embodiment of the present disclosure.
Figure 5B:
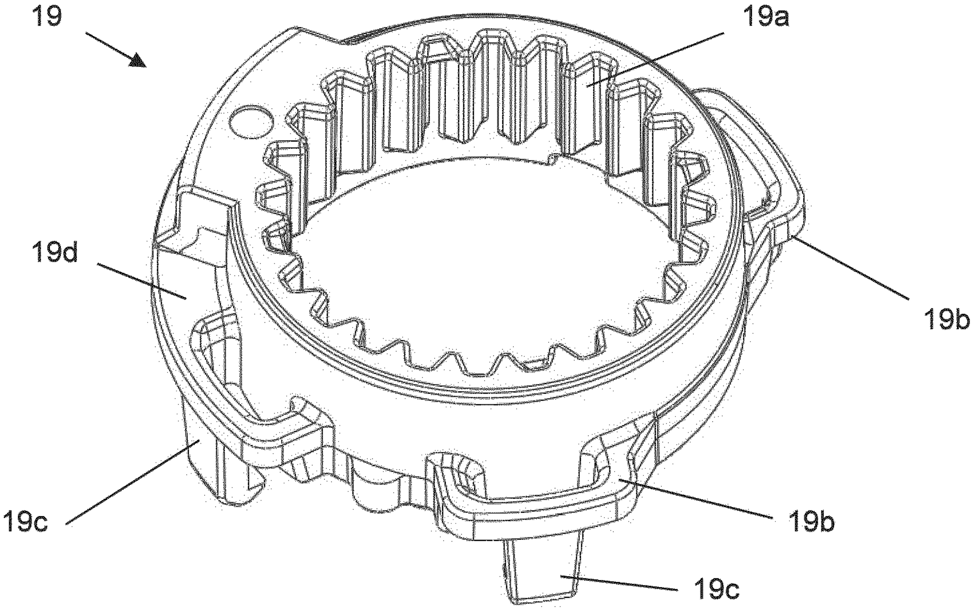
FIG. 5*b* shows a detail of the embodiment of FIG. 5*a*.

In the embodiment of FIGS. 5*a* and 5*b*, the insert 12 is partially formed as one single component part with the housing 10 and partially as a separate component part 19. The cup-shaped body 13 and the threaded tube 14 with the annular space for a compression spring are integrally formed with the housing 10 an connected thereto via arms 15, whereas the clutch feature 18 for rotationally constraining the drive sleeve 40 is a separate ring-shaped component part 19 which is axially and rotationally constrained to the housing 10. Thus, according to the embodiment of FIGS. 5*a* and 5*b*, the ring-shaped insert part 19 does not have the thread 17 as an integral part. As shown in FIG. 5*b* in more detail, the ring-shaped insert part 19 comprises axially orientated splines 19*a* on an inner surface to rotationally restrain the drive sleeve 40. The ring-shaped insert part 19 further comprises arms or splines 19*b* on its outer surface for rotational retention within the housing 10. Further, several hook-like arms 19*c* are provided to form a snap clip for axial retention of the ring-shaped insert part 19 within the housing 10. The ring-shaped insert part 19 comprises a hole or pocket 19*d* for receiving and fixing the hook end 91 of the drive spring 90. In addition, there are features on the ring-shaped insert part 19 that bias the insert parts 12, 19 axially and rotationally to remove free play.

The cartridge holder 20 is located at the distal side of housing 10 and may be permanently attached thereto. The cartridge holder may be a transparent or translucent component which is tubular to receive cartridge 100. The distal end of cartridge holder 20 may be provided with means for attaching a needle arrangement. A removable cap (not shown) may be provided to fit over the cartridge holder 20 and may be retained via clip features on the housing 10.

The piston rod 30 is rotationally constrained to the drive sleeve 40 via a splined interface. When rotated, the piston rod 30 is forced to move axially relative to the drive sleeve 40, through its threaded interface with the insert 12 of housing 10. The lead screw 30 is an elongate member with an outer thread engaging the corresponding thread of the insert 12 of housing 10. The interface comprises at least one longitudinal groove or track and a corresponding protrusion or spline of the driver 40. At its distal end, the lead screw 30 is provided with an interface for clip attachment of the bearing 140.

The drive sleeve 40 is a hollow member surrounding the lead screw 30 and arranged within number sleeve 60. It extends from an interface with the clutch plate 120 to the contact with the clutch spring 130. The drive sleeve 40 is axially movable relative to the housing 10, the piston rod 30 and the number sleeve 60 in the distal direction against the bias of clutch spring 130 and in the opposite proximal direction under the bias of clutch spring 130.

Figure 3A:
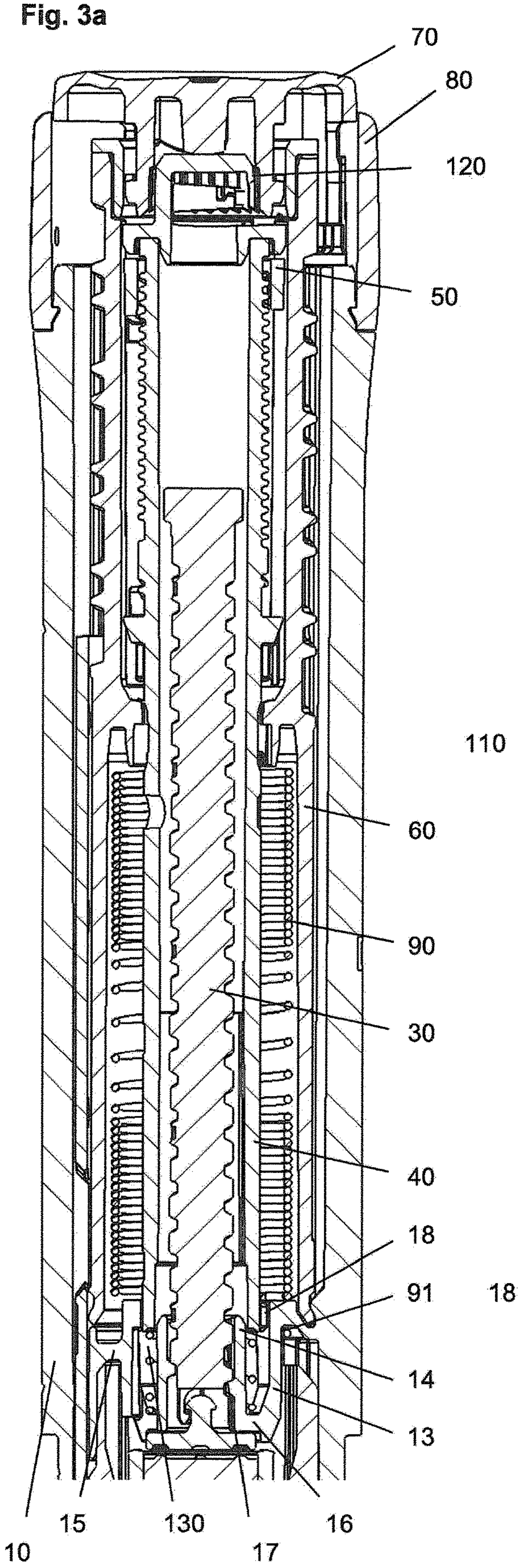
FIG. 3*a* shows a sectional view of the proximal end of the device of FIG. 1 in a dose setting state.

A splined tooth interface 18 with the insert 12 prevents rotation of the drive sleeve 40 during dose setting. This interface comprises a ring of radially extending outer teeth 41 at the distal end of drive sleeve 40 and corresponding radially extending inner teeth 18 of the housing component 10 (insert 12). When the button 70 is pressed (FIG. 3*b*), these drive sleeve to housing insert spline teeth are disengaged allowing the drive sleeve 40 to rotate relative to the insert and, thus, to housing 10. Clutch spring 130 biases the drive sleeve 40 into a position engaging with its teeth 41 the teeth 18 of the insert (FIG. 3*a*). A further splined tooth interface with the number sleeve 60 is not engaged during dialling, but engages when the button 70 is pressed, preventing relative rotation between the drive sleeve 40 and number sleeve 60 during dispense. In a preferred embodiment this interface comprises inwardly directed splines on a flange on the inner surface of the number sleeve 60 and a ring of radially extending outer splines of drive sleeve 40. These corresponding splines are located on the number sleeve 60 and the drive sleeve 40, respectively, such that axial movement of the drive sleeve 40 relative to the (axially fixed) number sleeve 60 engages or disengages the splines to rotationally couple or decouple the drive sleeve 40 and the number sleeve 60.

A further interface of the drive sleeve 40 comprises a ring of ratchet teeth located at the proximal end face of drive sleeve 40 and a ring of corresponding ratchet teeth on the clutch plate 120.

The driver 40 has a threaded section providing a helical track for the nut 50. In addition, a last dose abutment or stop is provided which may be the end of the thread or track or preferably a rotational hard stop for interaction with a corresponding last dose stop of nut 50, thus limiting movement of the nut 50 on the driver thread. At least one longitudinal spline of the driver 40 engages a corresponding track of the lead screw 30.

The last dose nut 50 is located between the number sleeve 60 and the drive sleeve 40. It is rotationally constrained to the number sleeve 60, via a splined interface. It moves along a helical path relative to the drive sleeve 40, via a threaded interface, expediently established by means of the helical track, when relative rotation occurs between the number sleeve 60 and drive sleeve 40 which, for the presently described mechanism is during dialling or setting only, where dose dialling refers to a dose setting operation. As an alternative, the nut 50 may be splined to the driver 40 and threaded to the number sleeve 60. A last dose stop is provided on nut 50 engaging a stop of drive sleeve 40 when a dose is set corresponding to the remaining dispensable amount of medicament or drug in the cartridge 100.

The dose indicator or number sleeve 60 is a tubular element. The number sleeve 60 is rotated during dose setting (via dose selector 80) and dose correction and during dose dispensing by torsion spring 90. Together with gauge element 110 the number sleeve 60 defines a zero position or zero dose position ('at rest') and a maximum dose position.

For manufacturing reasons the number sleeve 60 of the embodiment shown in the figures comprises a number sleeve lower 60*a* which is rigidly fixed to a number sleeve upper 60*b* during assembly to form the number sleeve 60. Number sleeve lower 60*a* and number sleeve upper 60*b* are separate components only to simplify number sleeve 60 mould tooling and assembly. As an alternative, the number sleeve 60 may be a unitary component. The number sleeve 60 is constrained to the housing 10 by snap engagement to allow rotation but not translation. The number sleeve 60 comprises an annular recess or groove near its distal end which engages a corresponding bead on an inner surface of the housing 10. The number sleeve lower 60*a* is marked with a sequence of numbers, which are visible through the gauge element 110 and the openings 11*a*, 11*b* in the housing 10, to denote the dialled dose of medicament.

Further, the number sleeve lower 60*a* has a portion with an outer thread engaging the gauge element 110. End stops are provided at the opposite ends of thread to limit relative movement with respect to the gauge element 110.

Clutch features which have the form of a ring of splines are provided inwardly directed on number sleeve upper 60*b* for engagement with splines of the button 70 during dose setting and dose correction. A clicker arm is provided on the outer surface of number sleeve 60 which interacts with the drive sleeve 40 and the gauge member 110 for generating a feedback signal. In addition, the number sleeve lower 60*a* is rotationally constrained to the nut 50 and to the clutch plate 120 via a splined interface comprising at least one longitudinal spline. Further, number sleeve lower 60*a* comprises an interface for attachment of the torsion spring 90.

The button 70 which forms the proximal end of the device is permanently splined to the dose selector 80. A central stem extends distally from the proximal actuation face of the button 70.

The stem is provided with a flange carrying the splines for engagement with splines of the number sleeve upper 60*b*. Thus, it is also splined via splines to the number sleeve upper 60*b* when the button 70 is not pressed, but this spline interface is disconnected when the button 70 is pressed. The button 70 has a discontinuous annular skirt with splines. When the button 70 is pressed, splines on the button 70 engage with splines on the housing 10, preventing rotation of the button 70 (and hence the dose selector 80) during dispense. These splines disengage when the button 70 is released, allowing a dose to be dialled. Further, a ring of ratchet teeth is provided on the inner side of button flange for interaction with clutch plate 120.

The dose selector 80 is axially constrained to the housing 10. It is rotationally constrained, via the splined interface, to the button 70. This splined interface which includes grooves interacting with spline features formed by the annular skirt of button 70 remains engaged irrespective of the dose button 70 axial positions. The dose selector 80 or dose dial grip is a sleeve-like component with a serrated outer skirt.

The torsion spring 90 is attached at its distal end by a hook 91 to the insert 12 and, thus, to the housing 10 and at the other end to the number sleeve 60. The torsion spring 90 is located inside the number sleeve 60 and surrounds a distal portion of the drive sleeve 40. The torsion spring 90 is pre-wound upon assembly, such that it applies a torque to the number sleeve 60 when the mechanism is at zero units dialled. The action of rotating the dose selector 80, to set a dose, rotates the number sleeve 60 relative to the housing 10, and charges the torsion spring 90 further.

The cartridge 100 is received in cartridge holder 20. The cartridge 100 may be a glass ampoule having a moveable rubber bung at its proximal end. The distal end of cartridge 100 is provided with a pierceable rubber seal which is held in place by a crimped annular metal band. In the embodiment depicted in the Figures, the cartridge 100 is a standard 1.5 ml cartridge. The device is designed to be disposable in that the cartridge 100 cannot be replaced by the user or health care professional. However, a reusable variant of the device could be provided by making the cartridge holder 20 removable and allowing backwinding of the lead screw 30 and the resetting of nut 50.

The gauge element 110 is constrained to prevent rotation but allow translation relative to the housing 10 via a splined interface. The gauge element 110 has a helical feature on its inner surface which engages with the helical thread cut in the number sleeve 60 such that rotation of the number sleeve 60 causes axial translation of the gauge element 110. This helical feature on the gauge element 110 also creates stop abutments against the end of the helical cut in the number sleeve 60 to limit the minimum and maximum dose that can be set.

The gauge element 110 has a generally plate or band like component having a central aperture or window and two flanges extending on either side of the aperture. The flanges are preferably not transparent and thus shield or cover the number sleeve 60, whereas the aperture or window allows viewing a portion of the number sleeve lower 60*a*. Further, gauge element 110 has a cam and a recess interacting with the clicker arm of the number sleeve 60 at the end of dose dispensing.

The clutch plate 120 is a ring-like component. The clutch plate 120 is splined to the number sleeve 60 via splines. It is also coupled to the drive sleeve 40 via a ratchet interface. The ratchet provides a detented position between the number sleeve 60 and drive sleeve 40 corresponding to each dose unit, and engages different ramped tooth angles during clockwise and anti-clockwise relative rotation. A clicker arm is provided on the clutch plate 120 for interaction with ratchet features of the button 70.

The clutch spring 130 is a compression spring. The axial position of the drive sleeve 40, clutch plate 120 and button 70 is defined by the action of the clutch spring 130, which applies a force on the drive sleeve 40 in the proximal direction. This spring force is reacted via the drive sleeve 40, clutch plate 120, and button 70, and when 'at rest' it is further reacted through the dose selector 80 to the housing 10. The spring force ensures that the ratchet interface between drive sleeve 40 and clutch plate 120 is always engaged. In the 'at rest' position, it also ensures that the button splines are engaged with the number sleeve splines, and the drive sleeve teeth are engaged with teeth of the housing 10.

The bearing 140 is axially constrained to the piston rod 30 and acts on the bung within the liquid medicament cartridge. It is axially clipped to the lead screw 30, but free to rotate.

With the device in the 'at rest' condition as shown in FIGS. 1 and 3*a*, the number sleeve 60 is positioned against its zero dose abutment with the gauge element 110 and the button 70 is not depressed. Dose marking '0' on the number sleeve 60 is visible through the window 11*b* of the housing 10 and gauge element 110, respectively.

The torsion spring 90, which has a number of pre-wound turns applied to it during assembly of the device, applies a torque to the number sleeve 60 and is prevented from rotating by the zero dose abutment.

The user selects a variable dose of liquid medicament by rotating the dose selector 80 clockwise, which generates an identical rotation in the number sleeve 60. Rotation of the number sleeve 60 causes charging of the torsion spring 90, increasing the energy stored within it. As the number sleeve 60 rotates, the gauge element 110 translates axially due to its threaded engagement thereby showing the value or size of the dialled dose, which may be a whole number multiple of a unit dosage increment or the minimum settable dose of the device, e.g. 11 U or 5 IU. A dose of up to 801 U may be set for example. The gauge element 110 has flanges either side of the window area which cover the numbers printed on the number sleeve 60 adjacent to the dialled dose to ensure only the set dose number is made visible to the user.

A specific feature of this embodiment is the inclusion of a visual feedback feature in addition to the discrete dose number display typical on devices of this type. The distal end of the gauge element 110 creates a sliding scale through the small window 11*a* in the housing 10. As an alternative, the sliding scale could be formed using a separate component engaged with the number sleeve 60 on a different helical track.

As a dose is set by the user, the gauge element 110 translates axially, the distance moved proportional to the magnitude of the dose set. This feature gives clear feedback to the user regarding the approximate size of the dose set. The dispense speed of an auto-injector mechanism may be higher than for a manual injector device, so it may not be possible to read the numerical dose display during dispense. The gauge feature provides feedback to the user during dispense regarding dispense progress without the need to read the dose number itself. For example, the gauge display may be formed by an opaque element on the gauge element 110 revealing a contrasting coloured component underneath. Alternatively, the revealable element may be printed with coarse dose numbers or other indices to provide more precise resolution. In addition, the gauge display simulates a syringe action during dose set and dispense.

The drive sleeve 40 is prevented from rotating as the dose is set and the number sleeve 60 rotated, due to the engagement of its splined teeth with teeth of the housing 10. Relative rotation must therefore occur between the clutch plate 120 and drive sleeve 40 via the ratchet interface.

The user torque required to rotate the dose selector 80 is a sum of the torque required to wind up the torsion spring 90, and the torque required to overhaul the ratchet interface. The clutch spring 130 is designed to provide an axial force to the ratchet interface and to bias the clutch plate 120 onto the drive sleeve 40. This axial load acts to maintain the ratchet teeth engagement of the clutch plate 120 and drive sleeve 40. The torque required to overhaul the ratchet in the dose set direction is a function of the axial load applied by the clutch spring 130, the clockwise ramp angle of the ratchet teeth, the friction coefficient between the mating surfaces and the mean radius of the ratchet interface.

As the user rotates the dose selector 80 sufficiently to increment the mechanism by one increment, the number sleeve 60 rotates relative to the drive sleeve 40 by one ratchet tooth. At this point the ratchet teeth re-engage into the next detented position. An audible click is generated by the ratchet re-engagement, and tactile feedback is given by the change in torque input required.

Relative rotation of the number sleeve 60 and the drive sleeve 40 is allowed. This relative rotation also causes the last dose nut/tracking member 50 to travel along its threaded path, towards its last dose abutment on the drive sleeve 40.

With no user torque applied to the dose selector 80, the number sleeve 60 is now prevented from rotating back under the torque applied by the torsion spring 90, solely by the ratchet interface between the clutch plate 120 and the drive sleeve 40. The torque necessary to overhaul the ratchet in the anti-clockwise direction is a function of the axial load applied by the clutch spring 130, the anti-clockwise ramp angle of the ratchet, the friction coefficient between the mating surfaces and the mean radius of the ratchet features. The torque necessary to overhaul the ratchet must be greater than the torque applied to the number sleeve 60 (and hence clutch plate 120) by the torsion spring 90. The ratchet ramp angle is therefore increased in the anti-clockwise direction to ensure this is the case whilst ensuring the dial-up torque is as low as possible.

The user may now choose to increase the selected dose by continuing to rotate the dose selector 80 in the clockwise direction. The process of overhauling the ratchet interface between the number sleeve 60 and drive sleeve 40 is repeated for each dose increment. Additional energy is stored within the torsion spring 90 for each dose increment and audible and tactile feedback is provided for each increment dialled by the re-engagement of the ratchet teeth. The torque required to rotate the dose selector 80 increases as the torque required to wind up the torsion spring 90 increases. The torque required to overhaul the ratchet in the anti-clockwise direction must therefore be greater than the torque applied to the number sleeve 60 by the torsion spring 90 when the maximum dose has been reached.

If the user continues to increase the selected dose until the maximum dose limit is reached, the number sleeve 60 engages with its maximum dose abutment on the maximum dose abutment of gauge element 110. This prevents further rotation of the number sleeve 60, clutch plate 120 and dose selector 80.

Depending on how many increments have already been delivered by the mechanism, during selection of a dose, the last dose nut 50 may contact its last dose abutment with stop face of the drive sleeve 40, e.g. an angular face. The abutment prevents further relative rotation between the number sleeve 60 and the drive sleeve 40, and therefore limits the dose that can be selected. The position of the last dose nut 50 is determined by the total number of relative rotations between the number sleeve 60 and drive sleeve 40, which have occurred each time the user sets a dose.

With the mechanism in a state in which a dose has been selected, the user is able to deselect or decrement any number of increments from this dose. Deselecting a dose is achieved by the user rotating the dose selector 80 anti-clockwise. The torque applied to the dose selector 80 by the user is sufficient, when combined with the torque applied by the torsion spring 90, to overhaul the ratchet interface between the clutch plate 120 and drive sleeve 40 in the anti-clockwise direction. When the ratchet is overhauled, anti-clockwise rotation occurs in the number sleeve 60 (via the clutch plate 120), which returns the number sleeve 60 towards the zero dose position, and unwinds the torsion spring 90. The relative rotation between the number sleeve 60 and drive sleeve 40 causes the last dose nut 50 to return along its helical path, away from the last dose abutment.

Figure 3B:
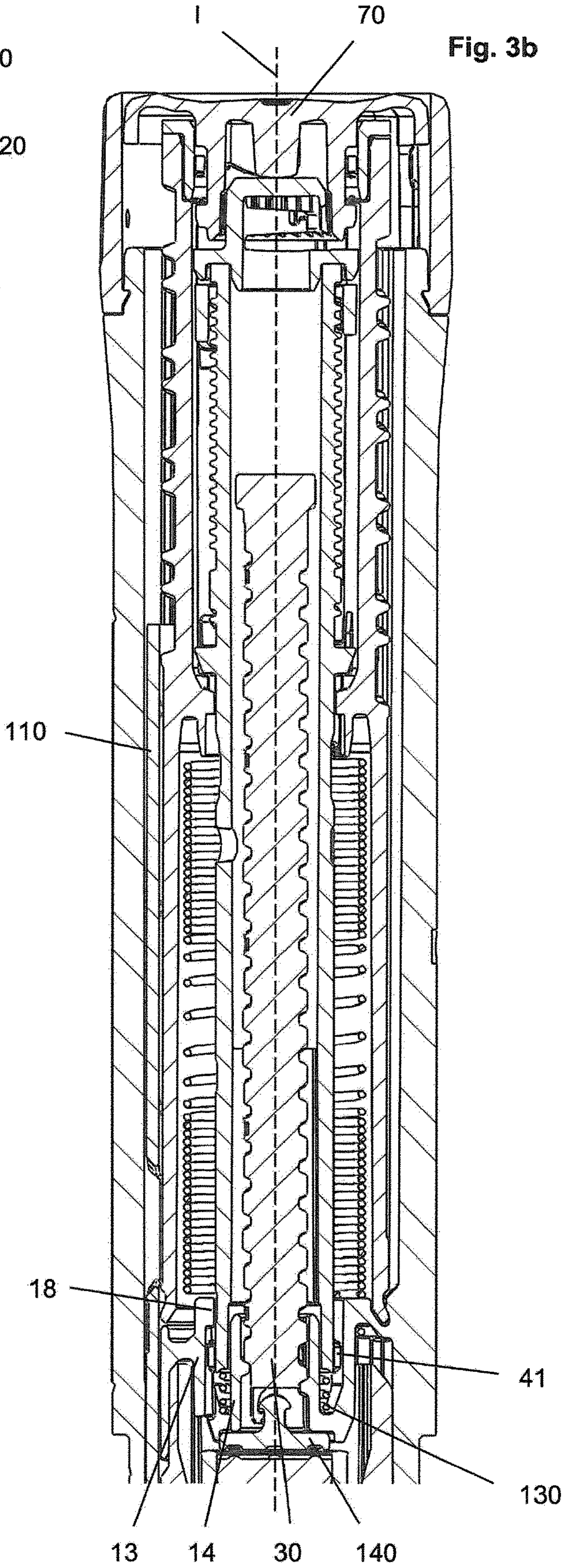
FIG. 3*b* shows a sectional view of the proximal end of the device of FIG. 1 in a dose dispensing state.

With the mechanism in a state in which a dose has been selected, the user is able to activate the mechanism to commence delivery of a dose. Delivery of a dose is initiated by the user depressing the button 70 axially in the distal direction (FIG. 3*b*).

When the button 70 is depressed, splines between the button 70 and number sleeve 60 are disengaged, rotationally disconnecting the button 70 and dose selector 80 from the delivery mechanism, i.e. from number sleeve 60, gauge element 110 and torsion spring 90. Splines on the button 70 engage with splines on the housing 10, preventing rotation of the button 70 (and hence the dose selector 80) during dispense. As the button 70 is stationary during dispense, it can be used in the dispense clicker mechanism. A stop feature in the housing 10 limits axial travel of the button 70 and reacts any axial abuse loads applied by the user, reducing the risk of damaging internal components.

The clutch plate 120 and drive sleeve 40 travel axially with the button 70. This engages the splined tooth interface between the drive sleeve 40 and number sleeve 60, preventing relative rotation between the drive sleeve 40 and number sleeve 60 during dispense. The splined tooth interface 18, 41 between the drive sleeve 40 and the housing insert 12 disengages, so the drive sleeve 40 can now rotate and is driven by the torsion spring 90 via the number sleeve 60, and clutch plate 120.

Rotation of the drive sleeve 40 causes the piston rod 30 to rotate due to their splined engagement, and the piston rod 30 then advances due to its threaded engagement to the housing 10. The number sleeve 60 rotation also causes the gauge element 110 to traverse axially back to its zero position whereby the zero dose abutment stops the mechanism.

Tactile feedback during dose dispense is provided via the compliant cantilever clicker arm integrated into the clutch plate 120. This arm interfaces radially with ratchet features on the inner surface of the button 70, whereby the ratchet tooth spacing corresponds to the number sleeve 60 rotation required for a single increment dispense. During dispense, as the number sleeve 60 rotates and the button 70 is rotationally coupled to the housing 10, the ratchet features engage with the clicker arm to produce an audible click with each dose increment delivered.

Delivery of a dose continues via the mechanical interactions described above while the user continues to depress the button 70. If the user releases the button 70, the clutch spring 130 returns the drive sleeve 40 to its ‘at rest’ or initial position (together with the clutch plate 120 and button 70), engaging the splines between the drive sleeve 40 and housing 10, preventing further rotation and stopping dose delivery.

During delivery of a dose, the drive sleeve 40 and number sleeve 60 rotate together, so that no relative motion in the last dose nut 50 occurs. The last dose nut 50 therefore travels axially relative to the drive sleeve 40 during dialling only.

Once the delivery of a dose is stopped, by the number sleeve 60 returning to the zero dose abutment, the user may release the button 70, which will re-engage the spline teeth between the drive sleeve 40 and housing 10. The mechanism is now returned to the ‘at rest’ condition.

At the end of dose dispensing, additional audible feedback is provided in the form of a 'click', distinct from the 'clicks' provided during dispense, to inform the user that the device has returned to its zero position via the interaction of the clicker arm on the number sleeve 60 with the ramp on the drive sleeve 40 and the cam and the recess on the gauge element 110. This embodiment allows feedback to only be created at the end of dose delivery and not created if the device is dialled back to, or away from, the zero position.

The drug delivery device discussed above is configured to deselect or decrement any number of dosage increments of a dose which has been set previously by incrementing the mechanism. The mechanism as disclosed above utilizes overhauling of a ratchet to decrease the set dose. This ratchet has to be able to withstand the continuously increasing torque exerted by the spring which increases with the size of the set dose, i.e. with the number of unit increments the dose comprises. Consequently, overhauling the ratchet may require significant force and/or generate significant noise.

When in the present disclosure it is referred to an "axial", "angular", "circumferential", or "radial" direction, the axis with respect to which these directions are specified may be an axis of the respective component or member, an axis of the housing, particularly a main longitudinal axis of the housing, the rotation axis around which the components or members rotate, and/or an axis of the drug delivery device, particularly the main longitudinal axis of the device. The axis may be oriented such that it extends through the proximal end and/or distal end of the device. Particularly, the proximal or distal direction may be parallel to and/or along the axis.

The housing is expediently static such that, if a component or member rotates and/or moves axially, it always moves relative to the housing. The respective component or member may be arranged such that they rotate about a common rotation axis, e.g. the longitudinal axis of the housing. The rotation axis may extend through the respective member.

The drug delivery device which has been discussed above comprises the nut 50 as a tracking member which is displaced along a guide track (helical thread) on the driver or drive sleeve 40 when a dose is set by rotating the number sleeve or dose indicator 60. Thus, referrals to the nut above and/or below may be considered as referrals to the tracking member. Referrals to the driver or drive sleeve 40 may be considered as referrals to a general drive member. Referrals to the dose setting member may be considered as referring to the dose selector 80. The driver 40 preferably engages the piston rod directly. The button 70 may be used as or correspond to an activation member which is used to initiate a dose dispensing operation as has been described previously when a dose has been set using the dose setting member. When the activation member is moved by the user, the mechanism may be switched from the dose setting mode of operation for the dose setting operation into the dose dispensing mode of operation for the dose delivery operation. By pressing the activation member, it is moved from a first or initial position to a second or dispense position which are axially, preferably only axially, offset from one another. When the activation member is released, it is moved back towards the initial position again, e.g. in the proximal direction. When the activation member or button is released it is moved back into the initial position by a spring, e.g. the clutch spring 130. In the mechanism discussed above, release of the activation member interrupts a dose dispensing procedure. Thus, the activation member has to be pressed during the entire dose dispensing procedure. The presently disclosed concepts do, however, also work for devices, where, once the activation member 70 has been pressed, the dose is dispensed without the option of interrupting the dose delivery operation, e.g. via releasing the activation member 70.

The distance of the tracking member 50 from an axial end position relative to the housing and/or as seen along the guide track or helical track of the driver 40 is characteristic for the amount of drug remaining in the cartridge 100 as has been discussed previously. The cartridge 100 comprises a cartridge body, e.g. of glass, and a bung which sealingly closes the proximal end of the cartridge body and, when moved towards the distal end of the cartridge body, dispenses liquid drug from the interior of the cartridge body through an opening in the cartridge or cartridge body, in particular when fluid communication is established between the interior of the cartridge and the exterior, e.g. by a needle unit comprising a needle. Without the needle, the distal end or dispensing end of the cartridge may be sealed by a septum. The septum may be pierceable by the needle of the needle unit which may be attached to a distal end of the cartridge holder 20. The cartridge holder 20 may be designed to receive the cartridge. The constituents of the cartridge are not explicitly shown in the drawings as is the needle unit.

In the embodiment which has been discussed further above, the tracking member 50, i.e. the last dose nut, has been arranged close to the interface where the driver 40 transfers force to the piston rod 30. Specifically, the tracking member was guided by a guide track on the driver 40. The tracking member 50 was driven by the number sleeve 60 during dose setting.

In the following, further embodiments of operating and/or arranging the tracking member within the drug delivery device or an arrangement for the drug delivery device are described. As opposed to the arrangement of the tracking member in FIGS. 1 through 5*b*, the tracking member will be arranged closer to the dose setting member as seen along the force transfer path from the dose setting member 80 to the tracking member 50. The embodiments below, consequently, provide (end-of-content) tracking mechanisms which may be used as an alternative to the mechanism described in conjunction with FIGS. 1 through 5*b*.

Figure 6A:
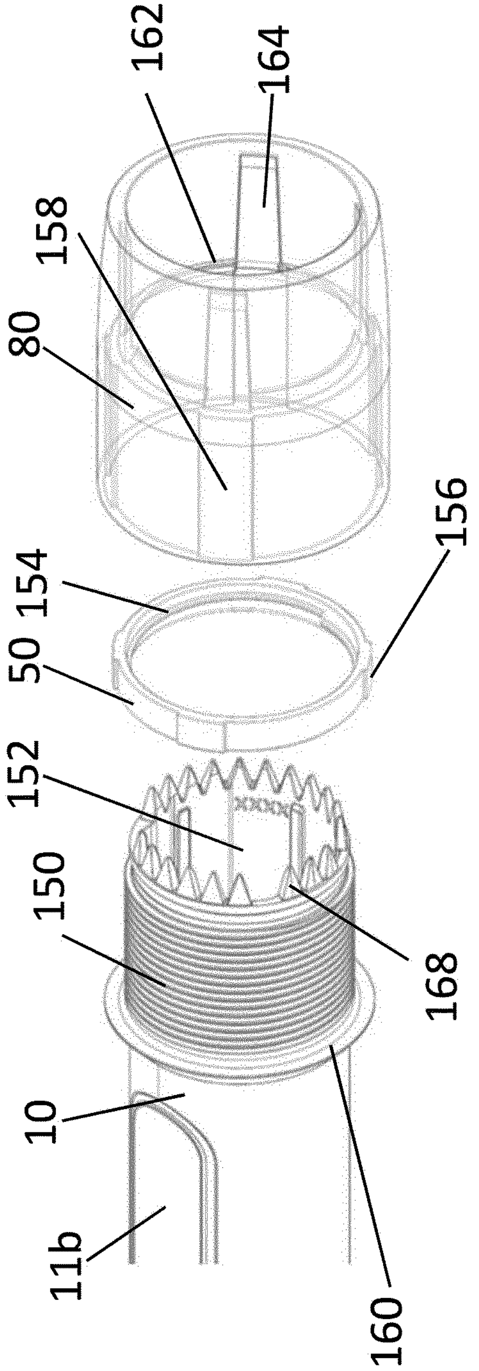
FIGS. 6*a* and 6*b* illustrate an exemplary embodiment of a drug delivery device
Figure 6B:
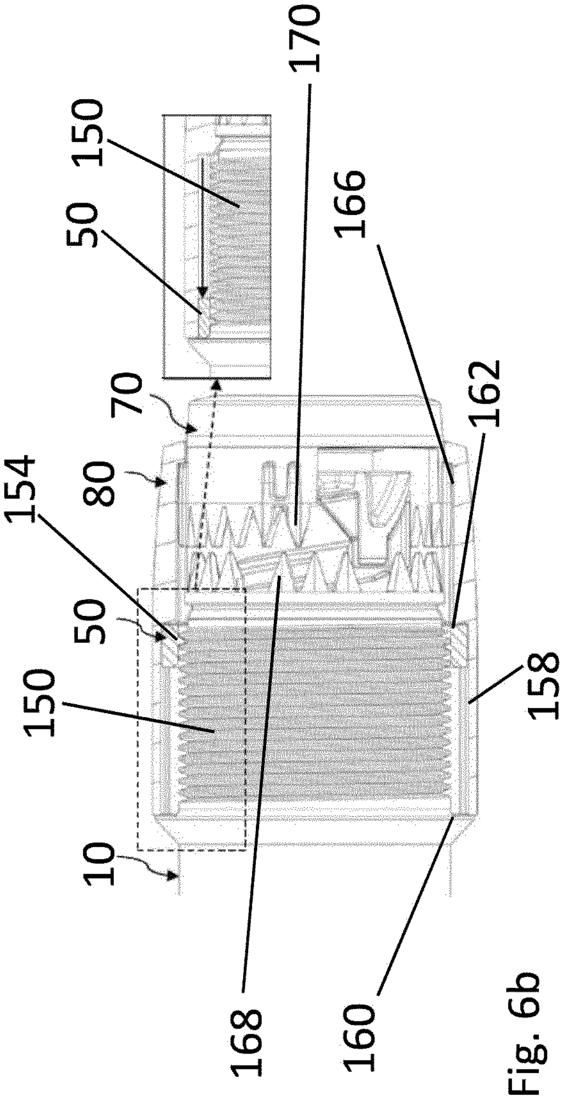

FIGS. 6*a* and 6*b* illustrate an exemplary embodiment of a drug delivery device, especially a drug delivery device comprising a tracking mechanism. FIG. 6*a* shows an exploded view of components or members of the drug delivery device involved in the operation of the mechanism. FIG. 6*b* illustrates the components or members when assembled. As the principal functionality of the device corresponds to the one which has been discussed further above in conjunction with FIGS. 1 through 5*b*, the following discussion focuses on the differences, although, of course, features which have been discussed above do also apply for the present embodiment.

The drug delivery device comprises the dose setting member 80. It further comprises the tracking member 50. It also comprises housing 10. Housing 10 may be the exterior housing of the drug delivery device as discussed further above. Especially, FIGS. 6*a* and 6*b* show the proximal end region of the housing and/or the drug delivery device. The tracking member 50 is configured as a nut. The tracking member 50 is arranged to engage a guide track 150, e.g. a helical thread. The guide track 150 may be provided on the housing 10. The guide track 150 is arranged in a proximal end region of the housing 10, e.g. adjoining a proximal opening 152 of the housing 10. The guide track 150 may be proximally offset from a window in the housing 10, e.g. from window 11*b*. The guide track 150 in the depicted embodiment, is provided on an outer surface of the housing 10. The tracking member 50 comprises a tracking member interaction feature 154, e.g. a protrusion, a thread or a part of a thread, which is arranged to engage the guide track 150. The tracking member 50 is rotationally locked to the dose setting member 80. For this purpose, the tracking member 50 and the dose setting member 80 comprise corresponding spline features 156 and 158. A plurality of corresponding spline features 156 and 158 may be provided circumferentially disposed around the respective member. The spline features are configured to prevent relative rotational movement between the dose setting member and the tracking member, expediently in both opposite rotational directions. Relative axial movement between the tracking member 50 and the dose setting member 80, however, is allowed. One or more protrusions as spline features 156 may be provided on an outer surface of the tracking member 50. Particularly, the protrusions may protrude in the radial direction. The corresponding spline features 158 may comprise indentations or slots in the dose setting member 80. In other words, in this embodiment, the tracking member 50 engages the housing 10 and the dose setting member 80. As in the previously described embodiment, the dose setting member 80 is axially secured to the housing 10 but rotatable relative to the housing. The axial fixation of the dose setting member to the housing is not explicitly shown in the drawings but may be implemented, e.g. by a circumferentially extending notch in the housing and a corresponding protrusion on the dose setting member engaging the notch. The activation member 70 may be partly received in the dose setting member. The activation member 70 may close a proximal opening of the dose setting member 80.

The housing 10, distally offset from the guide track 150, may comprise a radially outwardly directed protrusion or flange 160. The protrusion may provide a distal end stop for the tracking member 50. Alternatively or additionally, a rotational end stop may be provided on the housing 10, e.g. in the region of the flange 160. The rotational end stop may provide an angular surface which the tracking member 50 may have that in order to prevent further rotation. A proximal end stop for the tracking member 50 may be provided by a protrusion or flange 162 provided in the dose setting member 80.

The portion of the housing 10 which is received in the interior of the dose setting member 80 may have an axial extension which is greater than or equal to the axial extension of the guide track 150. The section of the dose setting member overlapping axially with the housing may be greater than or equal to 0.5 cm and/or less than or equal to 2.0 cm.

The spline features 158 may be provided in a distal portion of the dose setting member 80, e.g. distally from the protrusion 162. In a proximal portion of the dose setting member one or more further spline features 164 may be arranged. The button or activation member 70 (see FIG. 6*b*) is rotationally locked to the dose setting member 80 but axially movable relative thereto as has been discussed above already. For this purpose, spline features 164 may engage corresponding spline features 166 in the activation member 70. Merely as an example, the spline features 164 are radially oriented indentations and the spline features 166 are radially oriented protrusions.

The arrangement further comprises one or more locking features 168 and 170 which are configured to cooperate to lock the activation member 70 rotationally relative to the housing 10, especially when the dose delivery operation or dose dispensing operation has been initiated by pushing the activation member 70 distally. The respective locking features may be designed as teeth, which may be axially oriented and/or circumferentially disposed. When engaged, the teeth mesh and relative rotational movement is prevented in either rotational direction. When activation member is rotationally locked, so is the dose setting member 80. It is expedient to establish the rotational lock before the rotational coupling between the driver 40 and the number sleeve or dose indicator 60 is released for a dose delivery operation. Then, a risk that the dose setting member 80 and, consequently, the tracking member 50 is moved unintentionally is reduced.

FIG. 6*b*, in its left portion, shows the arrangement on the basis of a schematic sectional view in a dose setting state, where the dose setting member 80 can be rotated relative to the housing 10 in order to set a dose of a particular size to be delivered by the device. In the depicted situation, the tracking member 50 is in its initial position relative to the guide track 150, e.g. in a proximal initial position. That is to say no dose setting operation and also no dose delivery operation has been performed yet. If the dose setting member 80 is rotated, on account of the splined and threaded engagement with dose setting member and housing, the tracking member 50 travels axially relative to dose setting member 80 and housing 10 towards its axial end position, e.g. distally towards the flange 160. If the set dose is corrected, e.g. reduced by rotating the dosage in member in the opposite direction as during dose setting, the tracking member is displaced back towards its initial position. The number sleeve 60 may provide the zero dose abutment, e.g. in cooperation with an end stop on the housing, and, accordingly prevent a rotation of the dose setting member in that direction which would decrease the set dose in a situation when no dose has been set yet. This has been discussed above already in conjunction with the embodiment shown in FIGS. 1 to 5*b*.

In case the dose delivery operation is initiated by pressing the button or activation member 70 distally, i.e. to the left in FIG. 6*b*, the locking features 168 and 170 are brought into mechanical cooperation. Preferably, locking features 168 and 170 cooperate already before the rotational coupling between the number sleeve and the dose setting member is released, before the rotational lock of the driver 40 to the housing 10 is released, and/or before the driver 40 and the number sleeve 60 are brought into mechanical interaction to transfer the drive spring force from the number sleeve 60 to the driver 40. In this way, it can be ensured that the dose setting member 80 cannot be rotated in that direction counted the dose setting direction when the dose delivery operation has already been initiated. This ensures a precise position of the tracking member 50 relative to housing 10 and guide track 150 and particularly with respect to its axial end position. The clutch coupling acting between the dose setting member and the number sleeve for transferring rotation from the dose setting member to the number sleeve may be established via clutch features on the activation member engaging the number sleeve.

The portion of FIG. 6*b* on the right hand side shows the situation when the tracking member 50 has reached the axial end position, e.g. a distal end position. In this case, further increasing of the currently set dose is no longer possible since the rotation is blocked by the tracking member 150 abutting an end stop, e.g. flange 160 or a rotational end stop provided on the housing. Consequently, the tracking member blocks rotation of the dose setting member which would be required to increase the set dose.

During dose setting, when the dose setting member 80 is rotated, the rotation is transferred to the tracking member 50 on account of the rotational lock between the tracking member and the dose setting member. In other words, the rotation of the dose setting member is converted into axial displacement of the tracking member on account of the guide track 150 guiding movement of the tracking member. The movement of the tracking member is driven directly by the dose setting member. During the dose delivery operation, the activation member 70 is rotationally locked relative to the housing 10 on account of the locking features 168 and 170 engaging.

It should be noted that there is no need that the tracking member 50 travels distally during setting. It should be readily appreciated that the same functionality could also be realized with a tracking member which travels proximally towards an end position. Moreover, as will be readily appreciated, the guide track could also be provided on an inner surface of the dose setting member 70 instead of on an outer surface of the housing. In this case, spline features may be provided on the housing 10, e.g. on an outer surface thereof. This arrangement would result in the same kinematics of the dose setting member 80 driving axial displacement of the tracking member as the tracking member is rotationally locked to the housing and threadedly engaged with the dose setting member.

In the embodiment discussed above, the tracking member 50 interacts directly with the dose setting member 80 which forms a section or portion of the exterior surface of the drug delivery device. Further, the tracking member 50 directly interacts with the housing 10. Specifically, the tracking member 50 is arranged between the dose setting member 80 and the housing 10. A distal portion of the dose setting member 80 may be designed to receive the tracking member 50.

Figure 7A:
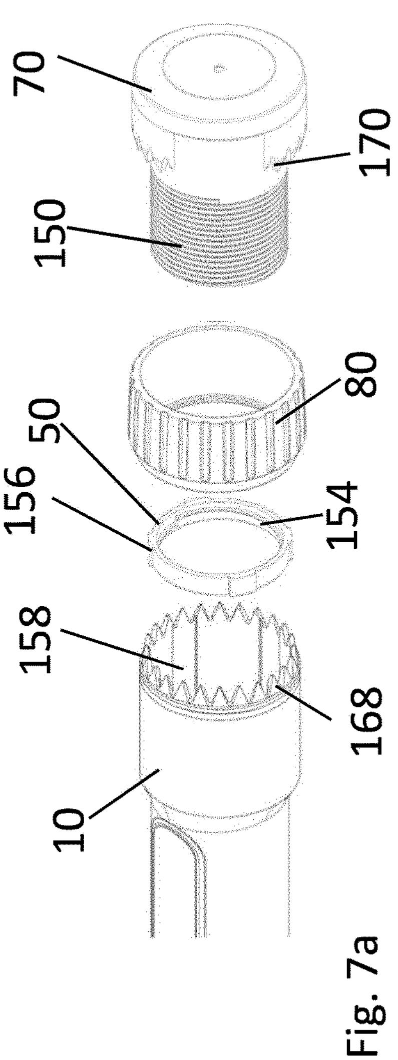
FIGS. 7*a* and 7*b* illustrate another exemplary embodiment of a drug delivery device.

FIGS. **7*a* and 7*b* illustrate another exemplary embodiment of a drug delivery device, especially comprising a tracking mechanism. Again, FIG. 7*a* shows an exploded view of components or members of the drug delivery device and FIG. 7*b*** shows the members in an assembled state on the basis of a schematic sectional view. The components or members involved in the mechanism are essentially the same as in the one discussed in the previous embodiment. Accordingly, the following description will focus on the differences. Of course, features disclosed in conjunction with the previous embodiment could be used in conjunction with this embodiment as well.

One difference to the previous embodiment is that the tracking member is arranged in the interior of the proximal end region of the housing 10. Spline features 158 are provided in this region of the housing. The proximal end region of the housing 10 may be wider than a region distally adjoining the proximal end region, e.g. a region between the proximal end region of the housing and window **11*b*. Between a more distal region and the proximal end region an inwardly directed step is provided in the housing on its exterior surface. This facilitates provision of an interior space of greater diameter which can receive the tracking member 50**. However, it should be noted that other shapes are possible as well.

The spline features 158 are provided to cooperate with the spline features 156 of the tracking member 50. The guide track 150 is provided on the activation member 70, e.g. on a distal and/or stem-like portion thereof. The guide track 150 may be arranged distally with respect to the locking features 170 of the activation member 70. Accordingly, in this embodiment, the tracking member is engaged with the activation member 70 and the housing 10. It is engaged with an outwardly facing surface of the activation member and an inwardly facing surface of the housing.

Figure 7B:
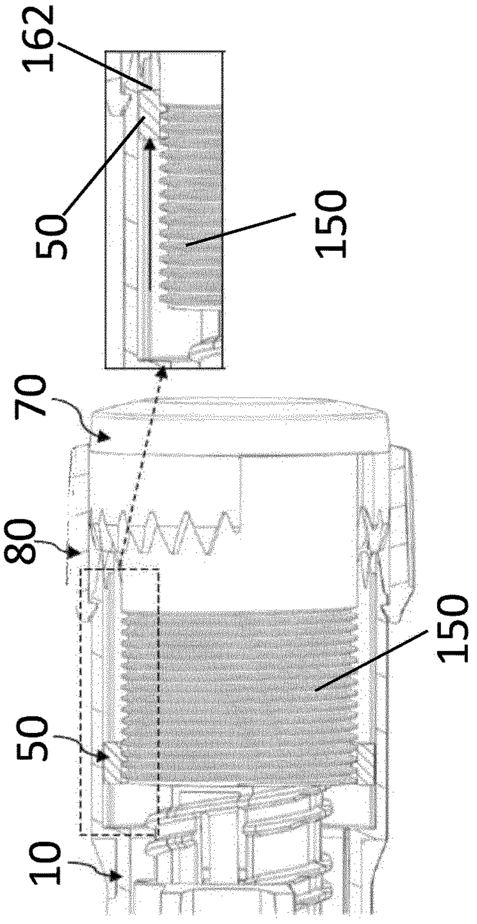

As depicted in FIG. **7*b*, the tracking member 50 is arranged between the activation member and the housing 10. In the initial position, e.g. when the cartridge is still full, the tracking member 50 may be arranged distally offset relative to a proximal end position which may be defined by a proximal end stop 162 as is apparent from the schematic representation of the situation when the tracking member is in its end position in the right part of FIG. 7*b* or by a rotational end stop. The proximal end position may be defined either by an axial stop or a rotational stop or by a combination of axial and rotational end stops. A rotational end stop may be formed by the end of the guide track 150 or by another end stop 162 separate from the track, e.g. provided on the activation member 70. The initial position of the tracking member is illustrated in the left part of FIG. 7*b*. In the representation of FIG. 7*b*, the axial lock of the dose setting member 80 with respect to the housing 10 is shown by way of a protrusion, which protrudes radially inwards from the dose setting member engaging a circumferential indentation or notch in the housing 10**. Of course, such an axial lock could also be implemented in a different manner.

During dose setting, on account of the rotational lock between the activation member 70 and the dose setting member 80, the activation member 70 rotates. This rotation drives the movement of the tracking member. For example, the activation member rotates relative to the tracking member 50 which, therefore, is displaced relative to the thread and axially relative to the housing on account of the splined connection to the housing which constrains relative rotation between the tracking member and the housing. In the depicted embodiment, the tracking member 50 travels proximally during dose setting towards the end position. Again as in the previous embodiment, it is also conceivable to have the tracking member 50 travel distally during dose setting towards its end position. During dose delivery, the dose setting member 80 is rotationally locked relative to the housing on account of the locking features 168 and 170 engaging as discussed previously already. Expediently, the rotational lock is established before the respective clutch engagement between activation member 70 and number sleeve 60 and/or between driver 40 and housing 10 is released. Again, the clutch features which rotationally lock the activation member to the number sleeve are not explicitly shown. When the activation member 70 is moved distally, so does the tracking member 50 due to the guide track being arranged on the activation member 70. The guide track 150 is expediently a self-locking thread. This is different from the embodiment in FIGS. **6*a* and 6*b*, where the movement of the activation member 70** does not have any effect on the position of the tracking member relative to the housing.

In its end position which is shown in the right portion of FIG. **7*b*, the dose setting member 80 cannot be rotated further to increase the dose since the activation member 70 is blocked from rotating by the tracking member 50 abutting end stop 162**, the tracking member being rotationally locked to the housing. Since the activation member is rotationally locked to the dose setting member this blocks rotation of the dose setting member in that direction which would increase the set dose. Consequently, this embodiment also provides for an end-of-content tracking mechanism or last dose stop mechanism as did the previously discussed embodiment.

As already mentioned for the previously described embodiment a reverse configuration is also possible in this embodiment where the tracking member is threadedly engaged to the housing and splined to the activation member. In most situations this is less preferable over the configuration depicted in the figures since manufacture of internal threaded surfaces is usually more difficult than externally or outer threaded surfaces, especially when the component is molded.

It should be noted, that at least some of the concepts, e.g. the one discussed in conjunction with FIGS. 7*a* and *b*, do also apply for dose setting members which are not axially locked to the housing, e.g. dose setting members which are axially displaced during the dose setting operation and/or during the dose delivery operation with respect to the housing. Rather, the concepts could also be used for dose setting members which are displaced relative to housing, particularly dose setting members which are displaced by a distance which is independent from or non-proportional to the size of the currently set dose and, preferably, constant for every dose delivery and/or dose setting operation.

Figure 8A:
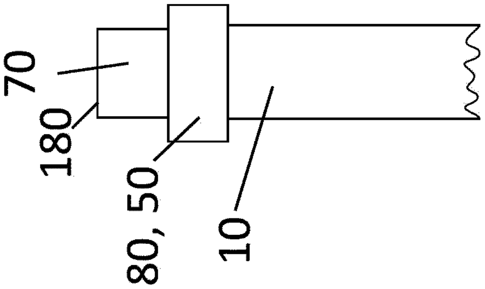
FIGS. 8*a* through 8*d* illustrate another exemplary embodiment of a drug delivery device.

FIGS. 8*a* through 8*d* schematically illustrate another embodiment of a drug delivery device, especially comprising a tracking mechanism. FIG. 8*a* illustrates a part of the drug delivery device including its proximal portion with the dose setting member 80, the housing 10, and the activation member 70. In this embodiment, the dose setting member 80 is used as tracking member 50. FIG. 8*a* shows the initial state of the device, where the tracking member 50 is in its initial axial position. In this initial state, neither a dose setting operation nor a dose delivery operation has been performed yet. The dose setting member 80 is, again, splined or rotationally locked to the activation member 70. As can be seen in the schematic sectional view of FIG. 8*c*, the tracking member 50/dose setting member 80 has a spline feature 172, e.g. a protrusion, which engages a corresponding spline feature 174, e.g. a slot, in the activation member 70.

As opposed to the embodiments which have been previously discussed, the dose setting member is not axially locked relative to the housing 10. Rather the dose setting member is threadedly coupled to the housing 10. Consequently, it is displaced relative to the housing, e.g. in the proximal direction or away from the distal end by a distance which is characteristic or proportional to the size of the set dose. In the depicted embodiment, a thread 176, e.g. a helical thread, is provided on the dose setting member, particularly an inner surface thereof, which interacts with an interaction feature 178 on the housing, particular an outer surface thereof. Of course, the position of the thread and the interaction feature 178 could also be reversed and/or both, dose setting member and housing could be provided with a thread, which are engaged with one another. The spline feature 172 crosses the housing 10 and, particularly a proximal end thereof in order to engage the activation member 70. The activation member 70 is arranged within the housing as seen in top view onto the proximal end. The dose setting member 80 is arranged outside of the housing and, particularly, the housing may be received partly in the dose setting member 80.

Since the dose setting member 80 is threadedly coupled to the housing 10, the axial position of the dose setting member relative to the housing changes as the set dose is increased. Preferably, the dose setting member moves into the proximal direction relative to the housing, i.e. away from the distal end of the housing, during the dose setting operation. By doing so, the distance between a proximal end face 180 of the activation member 70, is reduced, since the activation member 70 is axially static during dose setting. In the initial stage depicted in FIG. 8*a*, the distance by which the activation member 70 protrudes from the proximal end face of the dose setting member is greater than the total axial displacement distance of the tracking member 50 from its initial position into its axial tracking member end position, i.e. when the arrangement has performed dose delivery operations up to the maximum total dose (which is the sum of all deliverable doses) which the arrangement is configured to deliver.

Figure 8B:
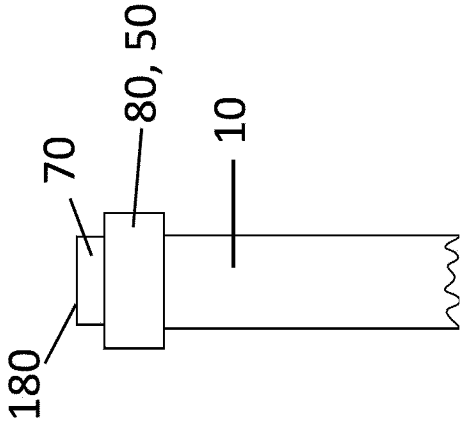
Figure 8C:
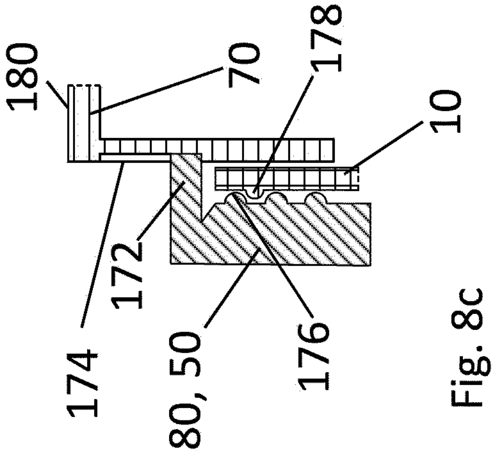

In the end position of the tracking member 50 or dose setting member 80, further rotation which would increase the size of the currently set dose is prevented. This position is depicted in FIG. 8*b*. As is apparent, the activation member 70 still protrudes proximally from the dose setting member 80 when the dose setting member has reached its axial end position. Preferably, this distance is still sufficient to allow movement of the activation number 70 in the distal direction relative to the dose setting member required to initiate the dose delivery operation, such as to release the clutch mechanism, e.g. by rotationally decoupling the number sleeve 60 and the dose setting member 80, coupling the driver 40 to the number sleeve 60 rotationally for the delivery operation and/or unlocking the driver 40 rotationally from the housing 10.

In order to ensure or prevent that, once a dose delivery operation has been triggered by pressing the activation member 70, rotation of the dose setting member 80 is expediently constrained during the dose delivery operation and/or when the activation member is being pressed. This enables that the position of the tracking member 50 relative to the tracking member axial end position does not change or cannot be changed during dose delivery easily and, consequently, the position of the tracking member always reflects the accumulated doses already dispensed from the device before the next setting operation is commenced.

Figure 8D:
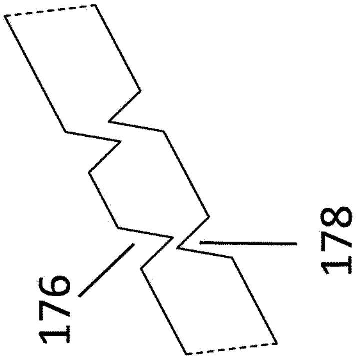

In the present embodiment, this can be achieved via a force transfer mechanism, e.g. a ratchet which still permits axial movement of the activation member into the position required for initiating the dose delivery operation. The force transfer mechanism may transfer a part of a distally directed axial force provided by the user for pressing the activation member 70 onto the interface between the thread 176 and the interface feature 178. In a very schematic fashion, this is illustrated in FIG. 8*d*. As depicted, axially oriented locking features are provided, which, when the thread 176 and the interaction feature 178 are moved axially towards one another, establish a rotational lock for the dose setting member 80 or tracking member 50 relative to the housing 10. The dose setting member 80/tracking member 50 is then no longer rotatable in either rotational direction relative to the housing 10.

All of the tracking mechanisms discussed in conjunction with FIGS. 6*a* through 8*d* guide the tracking member on a surface of comparatively large diameter. Moreover, the end stop blocking further rotation once the tracking member has reached its axial end position can be arranged at a relatively great diameter. Accordingly, the force acting on the end stop is comparatively small. Also, the load transferred to the tracking member may be reacted quickly by the housing and need not to be guided through further more sensible components of the dose setting and drive mechanism. Consequently, the proposed tracking mechanisms do have decisive advantages.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short—or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An examples of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

The scope of protection is not limited to the examples given herein above. The invention is embodied in each novel characteristic and each combination of characteristics, which particularly includes every combination of any features which are stated in the claims, even if this feature or this combination of features is not explicitly stated in the claims or in the examples.

| Reference numerals | |
|---|---|
| 10 | housing (casing) |
| 11a, b | window |
| 12 | insert |
| 13 | sidewall |
| 14 | tube |
| 15 | arm |
| 16 | bottom wall |
| 17 | thread |
| 18 | spline teeth |
| 19 | ring-shaped second part |
| 19a | spline teeth |
| 19b | arm (spline) |
| 19c | arm (snap clip) |
| 19d | opening |
| 20 | cartridge holder |
| 30 | piston rod (lead screw) |
| 40 | drive sleeve (drive member) |
| 41 | spline teeth |
| 50 | nut |
| 60 | number sleeve (dose indication member) |
| 60a | number sleeve lower |
| 60b | number sleeve upper |
| 70 | button |
| 80 | dose selector/dose setting member |
| 90 | torsion spring |
| 91 | hook |
| 100 | cartridge |
| 110 | gauge element |
| 120 | clutch plate |
| 130 | clutch spring |
| 140 | bearing |
| 150 | guide track |
| 152 | opening |
| 154 | interaction feature |
| 156 | spline feature |
| 158 | spline feature |
| 160 | protrusion |
| 162 | flange |
| 164 | spline feature |
| 166 | spline feature |
| 168 | locking feature |
| 170 | locking feature |
| 172 | spline feature |
| 174 | spline feature |

-continued

| Reference numerals | |
|---|---|
| 176 | thread |
| 178 | interaction feature |
| 180 | proximal end face |

The invention claimed is:

1. A drug delivery device comprising:
a housing having a proximal end and a distal end;
a dose setting member that is rotatable relative to the housing for a dose setting operation in order to set a dose of drug to be delivered;
a tracking member that either is operatively coupled or coupleable to the dose setting member;
a guide track configured to form a guiding interface to guide and/or drive movement of the tracking member,
wherein the tracking member is displaced towards an axial tracking member end position during the dose setting operation such that a distance by which the tracking member is displaced towards the axial tracking member end position depends on a size of a set dose
a setting clutch mechanism configured to couple the dose setting member to a further member during the dose setting operation,
wherein the setting clutch mechanism comprises a clutch force transfer interface via which force is transferred from the dose setting member to the further member in the dose setting operation, and
wherein the further member is rotationally locked to the dose setting member during the dose setting operation;
a tracking member force transfer interface,
wherein the force is transferred from the dose setting member to the tracking member via the tracking member force transfer interface; and
wherein the tracking member force transfer interface is arranged closer to an outer surface of the dose setting member than the clutch force transfer interface, and wherein force is transferred from the dose setting member to the further member via the clutch force transfer interface and along a force transfer path from the outer surface to the tracking member force transfer interface.

2. The drug delivery device of claim 1, wherein the tracking member force transfer interface is arranged proximally relative to the clutch force transfer interface.

3. The drug delivery device of claim 1, further comprising an activation member that is operable to perform a dose delivery operation for delivering a previously set dose, wherein the activation member is configured to be touched by a user for the dose delivery operation to move from a first position to a second position, wherein during the movement of the activation member from the first position to the second position
the setting clutch mechanism is released such that the dose setting member is decoupled from the further member, and/or
the dose setting member is rotationally locked relative to the housing.

4. The drug delivery device of claim 3, wherein the tracking member is engaged to the activation member.

5. The drug delivery device of claim 3, wherein the guiding interface is established between the tracking member and the activation member.

6. The drug delivery device of claim 1, wherein the dose setting member is rotationally locked relative to the housing before the setting clutch mechanism is released.

7. The drug delivery device of claim 1, wherein a position of the tracking member is fixed relative to the axial tracking member end position during a dose delivery operation that is performed subsequent to the dose setting operation.

8. The drug delivery device of claim 1, wherein the tracking member is arranged relative to the housing such that the tracking member overlaps with the dose setting member axially.

9. The drug delivery device of claim 1, wherein the tracking member is arranged between an outer surface of the housing and an inner surface of the dose setting member.

10. The drug delivery device of claim 1, wherein the dose setting member is axially locked to the housing but rotatable relative to the housing for the dose setting operation.

11. The drug delivery device of claim 1, wherein the dose setting member is engaged to the housing via the guide track.

12. The drug delivery device of claim 1, wherein the tracking member is engaged to the dose setting member.

13. The drug delivery device of claim 1, wherein the guiding interface is established between the tracking member and the housing.

14. The drug delivery device of claim 1, wherein the guiding interface is established between the tracking member and the dose setting member.

15. The drug delivery device of claim 1, wherein the tracking member is arranged in a proximal end region of the housing.

16. The drug delivery device of claim 1, further comprising a reservoir containing a drug.

17. The drug delivery device of claim 1, further comprising a reservoir retainer for retaining a reservoir containing a drug.

* * * * *